(12) United States Patent
Go et al.

(10) Patent No.: US 12,153,030 B2
(45) Date of Patent: Nov. 26, 2024

(54) METHOD FOR MEASURING A DEGREE OF HOMOGENEITY OF OILS USING BACK TITRATION AND MEASURING APPARATUS USING THE SAME

(71) Applicant: KOREA INSTITUTE OF ENERGY RESEARCH, Daejeon (KR)

(72) Inventors: Kang-Seok Go, Daejeon (KR); Nam-Sun Nho, Daejeon (KR); Kwang-Ho Kim, Daejeon (KR); Eun Hee Kwon, Daejeon (KR); Suk Hyun Lim, Jeonju-si (KR); Hung Hai Pham, Daejeon (KR); Anh Dung Pham, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 286 days.

(21) Appl. No.: 17/134,535

(22) Filed: Dec. 28, 2020

(65) Prior Publication Data
US 2021/0199633 A1    Jul. 1, 2021

(30) Foreign Application Priority Data
Dec. 30, 2019   (KR) .................. 10-2019-0177997

(51) Int. Cl.
*G01N 31/16* (2006.01)
*B01D 21/08* (2006.01)
*G01N 21/33* (2006.01)

(52) U.S. Cl.
CPC ............. *G01N 31/16* (2013.01); *B01D 21/08* (2013.01); *G01N 21/33* (2013.01); *B01D 2251/208* (2013.01); *B01D 2257/7027* (2013.01)

(58) Field of Classification Search
CPC .... G01N 21/33; G01N 33/2823; G01N 21/59; G01N 31/16; G01N 21/82; G01N 31/02; B03D 3/06; B01D 21/08; B01D 21/01
(Continued)

(56) References Cited

U.S. PATENT DOCUMENTS 4,628,204 A * 12/1986 Maes ................. G01N 33/2829
                                                    356/70
6,773,921 B1 * 8/2004 Schabron ............... C10G 11/18
                                                    436/163
(Continued)

FOREIGN PATENT DOCUMENTS

EP             892268 A1 *  1/1999  .......... G01N 31/164

OTHER PUBLICATIONS

Hotier, G. et al, Oil & Gas Science and Technology—Rev. IFP 1983, 38, 101-120.*
(Continued)

*Primary Examiner* — Arlen Soderquist
(74) *Attorney, Agent, or Firm* — CANTOR COLBURN LLP

(57) ABSTRACT

The present disclosure relates to an apparatus and a method for measuring miscibility in oil using back titration. The apparatus includes: a flocculation solution storage unit; a flow cell including a UV transmitting member; a dissolving agent storage unit; a UV irradiation unit; and a measurement unit, wherein: a flocculation solution is stored in the flocculation solution storage unit; the flocculation solution circulates between the flocculation solution storage unit and the flow cell; the measurement unit measures the UV transmittance of the flocculation solution while the dissolving agent in the dissolving agent storage unit is supplied to the flocculation solution storage unit; the miscibility in the oil is calculated from the amount of dissolving agent supplied and (Continued)

a change in the UV transmittance measured by the measurement unit; and the miscibility is calculated based on a time point when the slope of increase in the UV transmittance changes.

4 Claims, 3 Drawing Sheets

(58) Field of Classification Search
USPC .......................................................... 436/163
See application file for complete search history.

(56) References Cited

U.S. PATENT DOCUMENTS

| | | | | |
|---|---|---|---|---|
| 2004/0058451 | A1* | 3/2004 | Pauli ...................... | G01N 33/42 436/163 |
| 2005/0013740 | A1* | 1/2005 | Mason ............... | G01N 33/2811 422/68.1 |
| 2014/0375991 | A1* | 12/2014 | Schneider .............. | G01N 31/16 356/326 |
| 2019/0113473 | A1 | 4/2019 | Hascakir et al. | |

OTHER PUBLICATIONS

Griffith, M. G. et al, "Controlling Compatibility of Residual Fuel Oils" in: Marine Fuels, Jones, C. H. ed., Philadelphia, PA: American Society for Testing and Materials, 1985, 227-247.*
Andersen, S. I., Fuel Science and Technology International 1992, 10, 1743-1749.*
Chang, C.-L. et al, Langmuir 1994, 10, 1749-1757.*
Manek, M. B., SPE 28972, 1995, 9 pages.*
Rassamdana, H. et al, AIChE Journal 1996, 42, 10-22.*
Leontaritis, K. J., Fuel Science and Technology International 1996, 14, 13-39.*
Andersen, S. I. et al, Fuel Science and Technology International 1996, 14, 261-287.*
Andersen, S. I., Energy & Fuels 1999, 13, 315-322.*
Buckley, J. S., Energy & Fuels 1999, 13, 328-332.*
Peramanu, S. et al, Journal of Petroleum Science and Engineering 1999, 23, 133-143.*
Wiehe, I. A. et al, Energy & Fuels 2000, 14, 56-59.*
Wiehe, I. A. et al, Energy & Fuels 2000, 14, 60-63.*
Chow, R. et al, Journal of Canadian Petroleum Technology 2000, 39, 56-61.*
Lira-Galeana, C. et al, in "Asphaltenes and Asphalts, 2. Developements in Patroleum Science" 2000, Yen, T. F. et al (ed), 557-608.*
Peramanu, S. et al, Energy & Fuels 2001, 15, 910-917.*
Del Carmen Garcia, M. et al, Energy & Fuels 2001, 15, 1021-1027.*
Suzuki, O. et al, Jounal of the Japan Petroleum Institute 2002, 45, 207-213.*
Oh, K. et al, Energy & Fuels 2002, 16, 694-699.*
Alboudwarej, H. et al, Canadian International Petro;leum Conference 2002, paper 2002-015, 3 pages.*
Stark, J. L., Petroleum Science and Technology 2003, 21, 569-579.*
Aosmaning, S., Petroleum Science and Technology 2003, 21, 581-590.*
Karlsson, R. et al, Energy & Fuels 2003, 17, 1407-1415.*
Gharfeh, S. et al, Petroleum Science and Technology 2004, 22, 1055-1072.*
Ibrahim, H. H. et al, Fuel 2005, 84, 311-314.*
Rahmani, N. H. G. et al, Industrial & Engineering Chemistry Research 2005, 44, 75-84.*
Beck, J. et al, Energy & Fuels 2005, 19, 944-947.*
"Development of Petroleum Residua Solubility Measurement Methodology" Report WRI-06-P012, 2006, 33 pages.*
Kraiwattanawong, K. et al, Energy & Fuels 2007, 21, 1248-1255.*
Wiehe, I. A. et al, Energy & Fuels 2008, 22, 753-756.*
Huang, S.-C. et al, Road Materials and Pavement Design 2008, 9, 73-95.*
Kraiwattanawong, K. et al, Energy & Fuels 2009, 23, 1575-1582.*
Ocanto, O. et al, Energy & Fuels 2009, 23, 3039-3044.*
Neto, D. et al, Brazilian Journal of Petroleum and Gas 2009, 3, 149-157.*
Safieva, J. O. et al, Energy & Fuels 2010, 24, 2266-2274.*
Sinnathambi, C. M. et al, Journal of Applied Sciences, 2011, 11, 1815-1820.*
Burgass, R. et al, SPE 145946 2011, 10 pages.*
Juyal, P. et al, Energy & Fuels 2012, 26, 2631-2640.*
Schabron, J. F. et al, Energy & Fuels 2012, 26, 2256-2268.*
Passade-Boupat, SPE 164184 2013, 9 pages.*
Kamari, A. et al, Petroleum Science and Technology 2014, 32, 2837-2844.*
Rogel, E. et al, Energy & Fuels 2015, 29, 6363-6369.*
Stratiev, D. et al, Energy & Fuels 2015, 29, 7836-7854.*
Sieben, V. J. et al, Energy & Fuels 2016, 30, 1933-1946.*
Rehan, M. et al, Petroleum Science and Technology 2016, 34, 799-804.*
Guzman, R. et al, Fuel 2017, 188, 530-543.*
Rahimi, P., ACS Symposium Series "Chemistry Solutions to Challenges in the Petroleum Industry" 2019, 1320, 223-240.*
Novaki, L. P. et al, Energy & Fuels 2019, 33, 58-67 and 8 pages of Supplementary Information.*
ASTM D8253-20 2020, 12 pages.*
Van den Berg, F. G. A., Energy & Fuels 2022, 36, 8639-8648.*
Canadian Crude Quality Technical Association—Project—Crude Oil Compatibility 2022, 2 pages, downloaded from https://www.ccqta.com/projects.php?project_id=34.*
Hotier, G. et al, Oil & Gas Science and Technology—Rev. IFP 1983, 38, 101-120 with translation. (Year: 1983).*
Johnston, C. T. et al, Journal of Cosmetic Science 2003, 54, 113-118. (Year: 2003).*
Hu, C. et al, Chemical Engineering Science 2016, 140, 144-152 with 7 pages of supporting information. (Year: 2016).*
Zhang, J. et al., Colloids and Surfaces A: Physicochemical and Engineering Aspects 2016, 507, 1-6. (Year: 2016).*
Rassamdana, H. et al, Energy & Fuels 1999, 13, 176-187. (Year: 1999).*
Mohamed, R. S. et al, Protein Science and Technology 1999, 17, 877-896. (Year: 1999).*
Zhao, S. et al, Journal of Petroleum Science and Engineering 2004, 41, 233-242. (Year: 2004).*
Leyva, C. et al, Fuel Processing Technology 2013, 106, 734-738. (Year: 2013).*
Rahimi, P., ACS Symposium Series, "The Boduszynski Continuum: Contributions to the Understanding of the Molecular Composition of Petroleum" 2018, 1282, Chapter 8, 189-201. (Year: 2018).*
Saidoun, M. et al, Fuel 2019, 251, 523-533. (Year: 2019).*
Ekulu, G. et al, Journal of Dispersion Science and Technology 2004, 25, 321-331. (Year: 2004).*

\* cited by examiner

METHOD FOR MEASURING A DEGREE OF HOMOGENEITY OF OILS USING BACK TITRATION AND MEASURING APPARATUS USING THE SAME

CROSS-REFERENCE TO RELATED APPLICATION

This application claims priority to Korean Patent Application No. 10-2019-0177997, filed on Dec. 30, 2019, the disclosure of which is incorporated herein by reference in its entirety.

BACKGROUND ART

Technical Field

The present disclosure relates to a method and an apparatus for measuring miscibility in oil using back titration.

Description of the Related Art

In the process of processing crude oil and its fractions, a problem arises due to decreased miscibility. This problem corresponds to the separation of the wax component or asphaltene component in crude oil, and causes processing problems, including deposition in oil refining process equipment, fouling, and catalyst deactivation.

Asphaltene is frequently separated in the process of upgrading heavy oils such as vacuum residue through pyrolysis or hydrocracking.

In upgraded oil, asphaltene precipitation occurs due to a change in the composition of the oil. Asphaltene precipitation causes processing problems, including deposition in equipment, fouling, and catalyst deactivation. Thus, it is important to accurately measure the asphaltene stability of upgraded oil.

There is a D4870 method of measuring the total sediment content of residue. In this method, the sediment content is measured by hot filtration. However, this method has a problem in that measurement is not possible if the viscosity is high (55 cSt or higher at 100° C. or more) or the sediment content is high (0.5 wt % or higher).

Methods for measuring the dispersion stability of asphaltene include D6703, D7157 (S-value) and D7112 (P-value). However, these methods can measure dispersion stability only for crude oil, asphalt, and residual products, which have higher stability than upgraded oil. These methods have a problem in that, when upgraded oil is tested, clogging occurs or peak observation is impossible.

In the case of the conventional art D7157 (S-value), a high sediment content affects the measurement result, it has been suggested to perform measurement after removing insoluble substances through the D4870 method. However, this process has problems in that the representativeness of the sample is decreased due to loss of a certain portion of the sample, and errors in measurement occur due to filter clogging. Thus, the measurement method needs to be improved.

PRIOR ART DOCUMENTS

Patent Documents (Patent Document 0001) US Patent Application Publication No. 2019-0113473 (published on Apr. 18, 2019).

SUMMARY

An object of the present disclosure is to provide a method and an apparatus for measuring miscibility in oil using back titration.

However, technical objects to be achieved by the present disclosure are not limited to the above-mentioned technical problems, and other technical problems which are not mentioned herein can be clearly understood by those skilled in the art from the following description.

To achieve the above object, one aspect of the present disclosure provides an apparatus for measuring miscibility in oil using back titration, the apparatus including: a flocculation solution storage unit; a flow cell including a UV transmitting member; a dissolving agent storage unit; a UV irradiation unit configured to irradiate the UV transmitting member with UV light; and a measurement unit, wherein: a flocculation solution in which at least one of wax and asphaltene components of the oil is precipitated by a flocculant is stored in the flocculation solution storage unit; the flocculation solution circulates between the flocculation solution storage unit and the flow cell; the measurement unit measures the UV transmittance of the flocculation solution while the dissolving agent stored in the dissolving agent storage unit is supplied to the flocculation solution storage unit; the miscibility in the oil is calculated from the amount of dissolving agent supplied and a change in the UV transmittance measured by the measurement unit; and the miscibility is calculated based on a time point at which the slope of increase in the UV transmittance changes.

The component to be precipitated may be asphaltene, the flocculant may include a paraffin-based solvent, and the dissolving agent may include an aromatic-based solvent.

The UV transmittance may be stabilized using the flocculant before the measurement unit measures the UV transmittance of the flocculation solution.

The oil may have a sediment content of 0.5 wt % or more.

The oil may have a sediment content of 0.5 wt % to 20 wt %.

The oil may include crude oil, distilled oil, or upgraded oil.

The flocculant may include n-heptane, and the dissolving agent may include toluene.

The component to be precipitated may be wax, the flocculant may be a polar solvent, and the dissolving agent may be a paraffin-based solvent.

The flocculation solution storage unit may further include a stirring device.

Another aspect of the present disclosure provides a method for measuring miscibility in oil using back titration, the method including steps of: obtaining a flocculation solution by precipitating at least any one of wax and asphaltene components of the oil by a flocculant; measuring the UV transmittance of the flocculation solution while adding a dissolving agent to the flocculation solution; and calculating the miscibility in the oil from the amount of dissolving agent added and a change in the UV transmittance, wherein the miscibility is calculated based on a time point at which the slope of increase in the ultraviolet transmittance changes.

The component to be precipitated may be asphaltene, the flocculant may include a paraffin-based solvent, and the dissolving agent may include an aromatic-based solvent.

Measurement of the UV transmittance may be performed while the flocculation solution is circulated through the flow cell that measures the UV transmittance, and the method may further include a step of stabilizing the UV transmittance using the flocculant.

The oil may have a sediment content of 0.5 wt % or more.

The oil may have a sediment content of 0.5 wt % to 20 wt %.

The oil may include crude oil, distilled oil, or upgraded oil.

The flocculant may include n-heptane, and the dissolving agent may include toluene.

The component to be precipitated may be wax, the flocculant may be a polar solvent, and the dissolving agent may be a paraffin-based solvent.

DESCRIPTION OF SPECIFIC EMBODIMENTS

Hereinafter, the present disclosure will be described in more detail. However, the present disclosure may be embodied in a variety of different forms, and the scope of the present disclosure is not limited by the embodiments described herein and should be defined only by the appended claims.

In addition, terms used in the present disclosure are used only to describe specific embodiments, and are not intended to limit the present disclosure. Singular expressions include plural expressions unless specified otherwise in the context thereof. Throughout the present specification, "including" a certain component means further including other components rather than excluding other components unless otherwise specified.

A first aspect of the present disclosure provides an apparatus for measuring miscibility in oil using back titration, the apparatus including: a flocculation solution storage unit; a flow cell including a UV transmitting member; a dissolving agent storage unit; a UV irradiation unit configured to irradiate the UV transmitting member with UV light; and a measurement unit, wherein: a flocculation solution in which at least one of wax and asphaltene components of the oil is precipitated by a flocculant is stored in the flocculation solution storage unit; the flocculation solution circulates between the flocculation solution storage unit and the flow cell; the measurement unit measures the UV transmittance of the flocculation solution while the dissolving agent stored in the dissolving agent storage unit is supplied to the flocculation solution storage unit; the miscibility in the oil is calculated from the amount of dissolving agent supplied and a change in the UV transmittance measured by the measurement unit; and the miscibility is calculated based on a time point at which the slope of increase in the UV transmittance changes.

Hereinafter, the apparatus for measuring miscibility in oil according to the first aspect of the present disclosure will be described with reference to the accompanying drawings.

Figure 1:
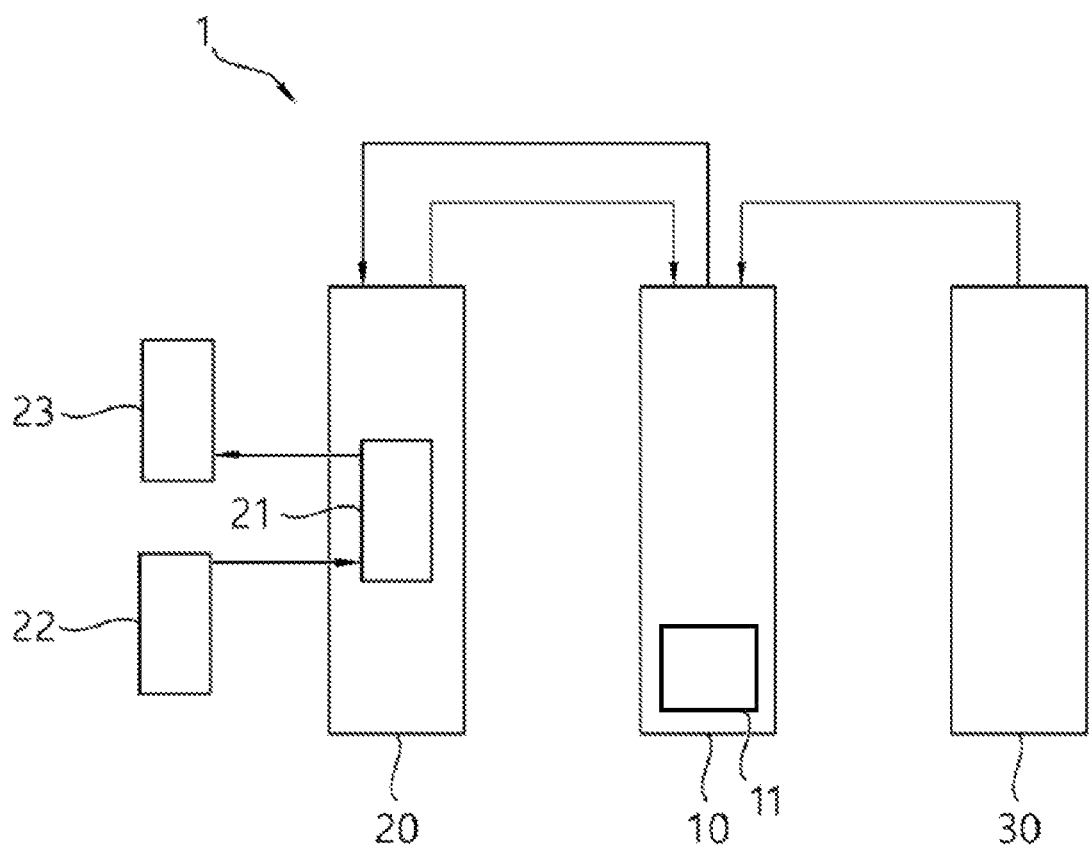
FIG. 1 is a schematic view showing an apparatus for measuring the miscibility of asphaltene in oil according to one embodiment of the present disclosure.

FIG. 1 is a schematic view an apparatus for measuring miscibility in oil according to one embodiment of the present disclosure.

In one embodiment of the present disclosure, a measurement apparatus 1 may include a flocculation solution storage unit 10, a flow cell 20, and a solvent storage unit 30.

As the flocculation solution storage unit or the dissolving agent storage unit, a storage container widely known in the art may be used without limitation. Preferably, a flocculation solution tank or a dissolving agent tank may be used.

In addition, in the drawings, elements such as a pump and a flow meter for fluid movement and control are omitted.

The flocculation solution circulates between the flocculation solution storage unit 10 and the flow cell 20. The flow cell 20 is provided with a UV transmitting member 21, preferably a UV transmitting window. A UV irradiation unit 22 irradiates the UV transmitting member 21 with UV light and a measurement unit 23 measures a UV transmittance of the flocculation solution.

The dissolving agent in the dissolving agent storage unit 30 may be supplied to the flocculation solution storage unit 10 by a metering pump. In one embodiment of the present Disclosure, a stirring device 11 may be provided in 10 the flocculation solution storage unit 10.

The principle of operation of the apparatus for measuring miscibility in oil according to the present disclosure will now be described with reference to the measurement method.

A second embodiment of the present disclosure provides a method for measuring miscibility in oil using back titration, the method including steps of: obtaining a flocculation solution by precipitating at least any one of wax and asphaltene components in the oil by a flocculant; measuring the UV transmittance of the flocculation solution while adding a dissolving agent to the flocculation solution; and calculating the miscibility in the oil from the amount of dissolving agent added and a change in the UV transmittance, wherein the miscibility is calculated based on a time point at which the slope of the increase in the ultraviolet transmittance changes.

Although detailed description of parts overlapping with those in the first aspect of the present disclosure is omitted in the second aspect of the present disclosure, description of the first aspect of the present disclosure may be equally applied to the second aspect of the present disclosure.

Hereinafter, the method for measuring miscibility in oil according to the second aspect of the present disclosure will be described with reference to the drawings.

Figure 2:
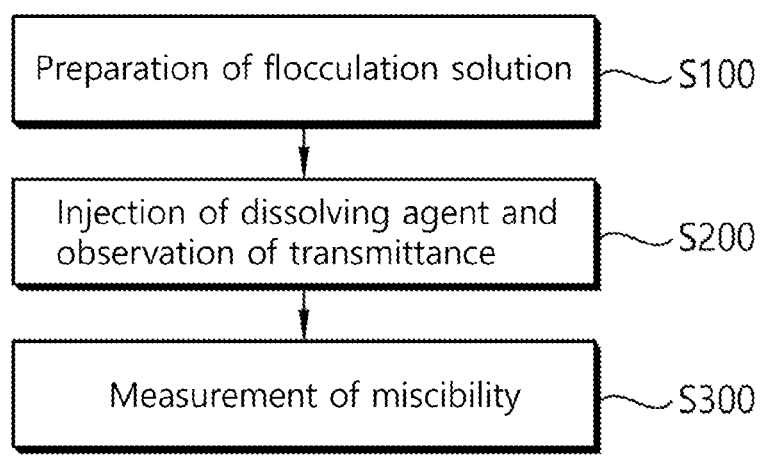
FIG. 2 is a flow chart showing a method for measuring the miscibility of asphaltene in oil according to one embodiment of the present disclosure.

FIG. 2 is a flow chart showing a method for measuring miscibility in oil according to one embodiment of the present disclosure.

First, a flocculation solution (precipitation solution) of oil is prepared (S100).

The object to be measured by the present disclosure is an oil containing wax or asphaltene. Asphaltene is defined as a material that is insoluble in n-pentane. The oil to be measured may be crude oil, distilled oil or upgraded oil, which contains wax or asphaltene components. The oil to be measured may be obtained by hydrocracking or pyrolysis of oil, but is not limited thereto.

The oil to be measured may have an asphaltene content of 0.5 wt % or more, specifically 0.5 wt % to 20 wt %.

A portion of wax or asphaltene forms sediments. The oil to be measured in the present disclosure may have a sediment content of 0.1 wt % or more (1.6 μm filter size [ASTM D4870]). The sediment content may be 0.1 wt % to 20 wt % or 0.5 wt % to 20 wt %, but is not limited thereto.

The flocculation solution is prepared by adding a flocculant to the oil. The flocculant may be a paraffin-based solvent or a polar solvent, specifically n-heptane, but is not limited thereto. Paraffin may be used for asphaltene, and a polar solvent may be used for wax.

The amount of flocculant used may be 20 to 60 times or 35 to 45 times the mass of the oil, but is not limited thereto. The flocculant may be added in excess so that the oil is sufficiently flocculated.

Thereafter, the UV transmittance of the flocculation solution is measured while a dissolving agent is added thereto (S200). The dissolving agent may be a paraffin-based solvent or an aromatic-based solvent, specifically toluene for asphaltene, but is not limited thereto. Before the measurement, only the flocculant may be used to stabilize the UV transmittance, and the UV transmittance of the flocculation solution may be stabilized.

The dissolving agent is added to the flocculation solution at a constant rate. Measurement of the UV transmittance of the flocculation solution is performed while the flocculation solution is passed through a flow cell.

Thereafter, the miscibility in the oil is calculated from the amount of dissolving agent used and the change in the measured ultraviolet transmittance (S300). The measured miscibility is a result calculated through the measured transmittance value, and the calculation may be performed and processed in an information processing device such as a computer.

As the amount of dissolving agent added increases, the UV transmittance begins to increase rapidly due to dissolution of the sediments (wax or asphaltene, etc.) of the flocculation solution, and when the sediments are completely dissolved, the UV transmittance increases slowly due to the dilution effect of the dissolving agent. When it is confirmed that the UV transmittance increases slowly, the experiment is terminated.

The miscibility in the oil may be calculated from the concentration of the flocculation solution (the amount of flocculant used/the amount of oil) and the amount of dissolving agent used until a time point at which the slope of increase (increase rate) in the UV transmittance decreases. A specific method for measuring the miscibility may be appropriately adjusted by those skilled in the art.

As the more stable oil, the amount of dissolving agent added decreases at a time point at which the slope of increase in the UV transmittance decreases.

According to the present disclosure, since the amount of the dissolving agent added when the increase rate of the UV transmittance changes, and the amounts of the sample and the flocculant are known, the solubility parameters for the oil and a time point at which the wax or asphaltene present in the oil dissolves may be derived.

In the derivation process, the volumetric mixing rule is used to calculate the volume of each component present in the solution, and the solubility parameters are obtained through an experiment because the solubility parameter values of the flocculant and the dissolving agent are known.

When the solubility parameter of the oil and the solubility parameter for a time point at which wax or asphaltene dissolves are derived, the miscibility may be determined as a quantitative value. Hereinafter, a method of processing back titration data will be described in detail.

According to the volumetric mixing rule, the product of the total solution volume (v) and the solubility parameter ($\delta$) of the mixture is equal to the sum of the products of the solution volume and the solubility parameter of each component (Equation 1 below).

$$v_{total}\delta_{mix} = \Sigma v_j \delta_j \quad \text{[Equation 1]}$$

The dissolving agent (e.g., toluene) solution volume may be expressed as the following Equation 2. In Equation 2 below, the onset point refers to an intersection point between a straight line that is an extension line of the slope before change and a straight line that is an extension line of the slope after change in a transmittance vs. time graph.

$$V_T = f(\text{toluene flow rate}) \times t(\text{onset time point}) \quad \text{[Equation 2]}$$

In addition, the solubility parameters of the mixture and the flocculant may be expressed as follows.

$$\delta_{mix} = v_{solvent}\delta^{solvent} + v_{oil}\delta_{oil}/(v_{solvent}+v_{oil}) \quad \text{[Equation 3]}$$

$$\delta_{floc} = (v_T\delta_T + v_H\delta_H + v_{oil}\delta_{oil})/(v_T+v_H+v_{oil}) \quad \text{[Equation 4]}$$

In Equations 3 and 4, $v_T$ is the solvent (e.g., toluene) solution volume, $v_H$ is the flocculant (e.g., n-heptane) solution volume, $v_{oil}$ is the volume of the oil, $\delta_T$ is the solubility parameter of the dissolving agent, $\delta_H$ is the solubility parameter of the flocculant, $\delta_{oil}$ is the solubility parameter of the oil, and $\delta_{floc}$ is the solubility parameter of the mixture at the flocculation onset point.

Thereafter, FR and 1/X are defined as in Equations 5 and 6 below and used as variables to obtain a 3-point plot with different concentrations. Then, the solubility parameter of the oil and the solubility at the flocculation onset point may be obtained through the Y-intercept and the slope as shown in Equation 7 below.

$$FR = v_T/(v_T+v_H) \quad \text{[Equation 5]}$$

$$1/X = W_{oil}/(v_T+v_H) \quad \text{[Equation 6]}$$

$$FR = \left[\frac{\delta_{floc}-\delta_H}{\delta_T-\delta_H}\right] - \left[\frac{\delta_{oil}-\delta_{floc}}{\delta_T-\delta_H}\right]\frac{1}{SG_{oil}X} \quad \text{[Equation 7]}$$

In Equations 5 to 7 above, FR denotes flocculation ratio (the ratio of the flocculant immediately before flocculation), $W_{oil}$ denotes the weight of the oil sample, $SG_{oil}$ denotes the specific gravity of the oil.

According to the present disclosure, even for oil which requires pretreatment such as filtering due to the high sediment content thereof, the miscibility of wax or asphaltene in the oil may be easily calculated without separate treatment.

Unstable oil has strong cohesiveness, and thus is flocculated immediately when being titrated with a flocculant, making it difficult to determine the flocculation onset point thereof. In the present disclosure, in order to measure the miscibility in of this unstable oil, a back titration method was developed in which a sample is first flocculated and the time point at which the sediments are dissolved by addition of a dissolving agent is observed.

Hereinafter, the present disclosure will be described in more detail with reference to an experimental example. In the Experimental Example, an experiment was performed on asphaltene.

As a UV device, Shimadzu UV-2700 (740 nm) was used, and as a flow cell, Starna type 74.4 (Quarz) was used. Injection of a dissolving agent was performed using a Teledyne D-series syringe pump was used.

First, n-haptane was circulated through the flow cell 20 to set the zero point (100% transmittance) of the UV device. After oil and n-haptane were added to a vial and then mixed together at 500 rpm and 20° C. to generate sediments. The flocculation solution was injected into a flocculation solution tank 10 and circulated through the flow cell 20 to stabilize UV transmittance.

After the UV transmittance is stabilized, the UV transmittance was observed while toluene in the dissolving agent tank 30 was injected (titrated) into the flocculation solution tank 10 by a metering pump. When it was confirmed that the sediments were completely dissolved and the slope of increase in the UV transmittance was changed by the dilution effect of the toluene, the experiment was terminated In the experiment, 0.05 g of the oil and 3 ml of n-heptane were used, and toluene was supplied at a rate of 0.3 ml/min. As the oil, each of vacuum residue (VR) and an upgraded oil produced by hydrocracking vacuum residue was used.

The vacuum residue was obtained from an oil refinery company and had the following composition: 20.1% VGO (343 to 524° C.) and 79.9% VR (524° C.).

The upgraded oil was obtained by hydrocracking the vacuum residue at 435° C. and 160 bar for 2 hours. The upgraded oil had an asphaltene content of 7.8 wt % and a sediment content of 1.6 wt %.

In the experiment, the UV path length was 0.5 mm.

Figure 3:
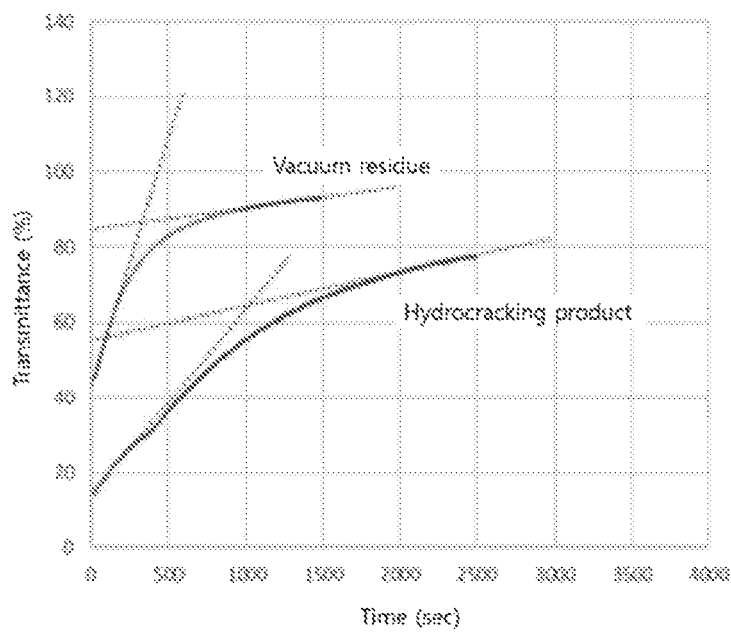
FIG. 3 shows the change in transmittance of each of vacuum residue and upgraded oil by injection of a dissolving agent in an experimental example of the present disclosure.

FIG. 3 shows the change in transmittance of each of vacuum residue and upgraded oil by injection of a dissolving agent in the experimental example of the present disclosure.

It can be seen that the time point at which the slope of increase in the transmittance of each of the vacuum residue (VR) and the upgraded oil (product) changes can be clearly determined. In addition, looking at the time point at which the slope changes, that is, the sediments are completely dissolved, it can be seen that the upgraded oil requires more toluene supply than the vacuum residue, suggesting that the upgraded oil is more unstable than the vacuum residue.

For wax, a polar solvent is used as a flocculant, and a paraffin solvent is used as a dissolving agent.

As described above, the present disclosure provides a method and an apparatus for measuring miscibility in oil using back titration. In particular, the present disclosure provides a method and an apparatus for measuring miscibility which minimizes sample loss or measurement error without filtering for an oil which requires filtering due to the high sediment content thereof.

The effects of the present disclosure are not limited to the above effects, and should be understood to include all effects that can be deduced from the configuration of the present disclosure described in the detailed description or the appended claims.

The present disclosure described above is not limited by the above-described embodiments and the accompanying drawings, and it will be obvious to those skilled in the art that various substitutions, modifications and changes are possible without departing from the technical spirit of the present disclosure.

What is claimed is:

1. An apparatus A method for measuring miscibility in oil using back titration, the apparatus method comprising:
    obtaining a flocculation solution comprising
        an oil, the oil comprising asphaltene, and
        a flocculant to precipitate the asphaltene,
            wherein an amount of the flocculant in milliliters in the flocculation solution is 20 to 60 times a mass of the oil in grams in the flocculation solution;
    measuring a UV transmittance of the flocculation solution while adding a dissolving agent to the flocculation solution; and
    calculating the miscibility in the oil from the amount of dissolving agent added and a change in the UV transmittance,
    wherein the miscibility is calculated based on a time point at which a slope of increase in the ultraviolet transmittance changes,
    wherein the oil has an asphaltene content of 0.5 wt % to 20 wt %, and
    wherein the oil is upgraded oil.

2. The method of claim 1, wherein the flocculant is n-heptane, and the dissolving agent is toluene.

3. The method of claim 1, wherein an amount of the flocculant in milliliters in the flocculation solution is 35 to 45 times a mass of the oil in grams in the flocculation solution.

4. The method of claim 1, wherein the oil is upgraded oil produced by hydrocracking vacuum residue.

* * * * *